United States Patent [19]

Casini et al.

[11] Patent Number: 4,978,772
[45] Date of Patent: Dec. 18, 1990

[54] UTILIZATION OF OTILONIUM BROMIDE (DCI) FOR TOPICAL APPLICATION IN THE GASTROINSTESTINAL TRACT AND RELATED PHARMACEUTICAL FORMULATION APPROPRIATE FOR SUCH USE

[75] Inventors: Alessandro Casini, Florence; Sandro Parti, Valdarno; Paolo Bucci, Montevarchi, all of Italy

[73] Assignee: A. Menarini S.A.S., Florence, Italy

[21] Appl. No.: 117,751

[22] Filed: Nov. 4, 1987

[30] Foreign Application Priority Data

Nov. 4, 1986 [IT] Italy ................................ 9514 A/86

[51] Int. Cl.$^5$ ............................................ C07C 229/00
[52] U.S. Cl. ........................................ 560/45; 560/46; 128/4
[58] Field of Search ........................ 560/45, 46; 128/4

[56] References Cited

PUBLICATIONS

Maggi et al., "Assessment of Potential Selectively of Antispasmodics for the Various Sections of the Gastrointestinal Tract of the Rat As A Guideline for Their Clinical Use", Arch. Int. Pharmacodyn. Thes., 262(2), pp. 221–230, Chemical Abstract No. CA99(3):16367e.

Baldi et al., "Effect of a New Antispasmodic Drug, Otilonium Bromide, on the Motor Activity of the Human Gastric Antrum", Clin. Ter. (Roms), 94(2), pp. 159–163, Chemical Abstract No. CA94(5):25196X.

Scarpignato et al., "Effects of Otilonium Bromide on the Gastrointestinal Tract in Vivo", Farmaco, Ed. Prat., 35(5), pp. 249–257, Chemical Abstract No. CA93(5):37410e.

Zappia et al., "Spasmolytic Effect of Otilonium Bromide on Gastrointestinal Motility", Farmaco, Ed. Prat., 35(5), pp. 258–264, Chemical Abstract No. CA93(5):36995n.

Primary Examiner—William R. Dixon, Jr.
Assistant Examiner—Anthony J. Green
Attorney, Agent, or Firm—McGlew and Tuttle

[57] ABSTRACT

Use of bromure d'otilonium, that it otilonii bromidum, for local applications in the gastrointestinal tract of the digestive system and related pharmaceutical formulation appropriate for such use, to obtain the arrest of the motility of the gastrointestinal tract in order to allow endoscopic manoeuvers for diagnostic and therapeutic purposes.

19 Claims, No Drawings

UTILIZATION OF OTILONIUM BROMIDE (DCI) FOR TOPICAL APPLICATION IN THE GASTROINSTESTINAL TRACT AND RELATED PHARMACEUTICAL FORMULATION APPROPRIATE FOR SUCH USE

FIELD OF THE INVENTION

The present invention relates to a specific utilization of bromure d'otilonium DCI, that is otilonii bromidum:

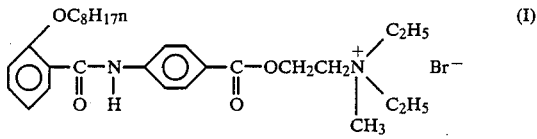

and to a related pharmaceutical formulation particularly suitable for preparation and for administration.

BACKGROUND OF THE INVENTION

Otilonium bromide is a myolytic active substance which has been used for some time in clinical practice, by oral administration, for the therapy of spastic-dyskinetic forms of the digestive or alimentary canal both on a functional and organic basis.

SUMMARY AND OBJECTS OF THE INVENTION

It is an object of the present invention to use said product in a pharmaceutical formulation which is suitable to effect a local application (installation or nebulization) in the gastrointestinal tract. By provoking an immediate arrest of the motility of the digestive or alimentary canal at the sprinkling point, said use will allow endoscopic maneuvers both for diagnostic and therapeutic purposes (bioptic sampling, removal of polypoid formations, and others).

More particularly, an object of the invention is pharmaceutical form comprising a bottle containing otilonium bromide and appropriate excipient and a solvent vial containing sterile water. At the time of utilization, the contents of the solvent vial are transferred to the small vial containing the active principle which is thus solubilized. Said solution can be used with a suitable apparatus for instillation or nebulization inside the gastrointestinal canal or tube.

DESCRIPTION OF THE PREFERRED EMBODIMENT

The conservation of the active principle in a dry state is due to stability demands In fact, otilonium bromide cannot be kept in solution for long, as this would cause its degradation.

The pharmaceutical composition which is the object of the invention comprises, further to the above-defined active principle, several excipients for specific functions inherent in the above utilization.

Fundamental excipients of the above pharmaceutical form are an antifoaming compound and one or more emulsifying compounds which assist the antifoaming compound. Said formulation prevents formation of foam on instillation or nebulization of the water solution of otilonium bromide, once obtained, thus allowing a clear endoscopic vision of the bowels.

Fundamental excipients of the above pharmaceutical form can be: one or more antifoaming compounds such as linear chain primary amine salt compounds (for example tetradecylamine acetate), sulfonated oils, aklylphenylglycolethers, primary alcohols with more than five carbon atoms, polyethyleneglycols, methylic or phenylic derivatives of polysiloxane and mixtures of same; and one or more emulsifying compounds such as sugar esters (for example sucrose stearate, palmitate and others), sorbitanesters of fatty acids (such as sorbitanmonostearate, -monopalmitate, -monooleate, and others), polyoxyethylenesorbitanesters of fatty acids (such as polyoxyethylenesorbitan-monopalmitate, -monostearate, -monooleate, and others), polyoxyethylenic esters of fatty acids (such as polyoxyetilene-stearate, laurate, -palmitate and others), polyoxyethylenic esters of superior, i.e. higher, alcohols (such as polyoxyethylenelaurylether, -stearylether, -cetylethere, -oleylether and others), fatty acid esters (such as glycerylstearate, glycerylpalmitate, glyceryloleate, cetylpalmitate, ethyleneglycolstearate, polyethylenoglycolstearate, propyleneglycolstearate, and others).

Said formulation prevents the formation of foaming on instillation, which advantageously assists endoscopic operations.

The preparation of the powder mixture contained in the bottle is carried out by solubilization in an appropriate inert solvent, such as methylene chloride, chloroform, acetone, etc., the excipient being provided in such a manner as to reach a concentration between 15% and 30%. Subsequently, said solution is made to be absorbed in a homogeneous way on the active principle utilizing a suitable apparatus. The mixture thus obtained is desiccated in an appropriate manner until the total elimination of the solvent.

Alternatively, the preparation of the above mixture can be carried out by allowing the various excipients, previously mixed and melted, to be absorbed on the active principle by using an appropriate apparatus.

The following formulations are given as unrestrictive examples:

| | |
|---|---|
| otilonium bromide | 10–300 mg and preferably 150 mg |
| dimethylpolysiloxane | 0.3–10 mg and preferably 5 mg |
| glycerylmonostearate | 0.01–0.5 mg and preferably 0.25 mg |
| sorbitanemonopalmitate | 0.08–2.5 mg and preferably 1.25 mg |
| sucrose monopalmitate | 0.01–0.5 mg and preferably 0.25 mg |
| water | 12–18 ml and preferably 15 ml |

Clinical experiments using the pharmaceutical form of the composition of the above specific example comprised the nebulization or the instillation inside the bowels (colon or stomach) or the instillation in the esophagus, before clinical examination, using common endoscopy apparatus in subject presenting such functional dyskinetic affections of the esophagus and of the gastroenteric system as to require an endoscopic examination for diagnostic purposes. Said endoscopic examination turned out particularly easy due to the immediate arrest of the motility of the bowel under observation, and the effectiveness of the formulation has always been satisfactory, due both to the possibility of an extempore preparation of the solution and to the presence of the antifoaming and emulsifying excipients.

We claim:

1. Method of using on a subject a pharmaceutical product based on otilonium bromide as active principle, which comprises the step of applying topically by an endoscopic instrument, at a selected location inside the gastrointestinal tract of the subject, a composition formed comprising said active principle, one or more antifoaming excipients and one or more emulsifying excipients.

2. Method of claim 1 wherein said step of applying topically at a selected location inside the gastrointestinal tract of the subject includes locally applying by instillation or nebulization in the digestive or alimentary canal.

3. Method of claim 1 wherein the composition is provided in liquid form and said step of applying topically at a selected location inside the gastrointestinal tract of the subject includes topically applying to assist endoscopic procedures for at least one of diagnostic and therapeutic purposes.

4. Method of claim 1 wherein the composition is an aqueous solution containing the active principle, and the anti-foaming and emulsifying excipients.

5. Method of claim 1 wherein the composition is formed corresponding to the following formulation

| [bromure d'otilonium] otilonium bromide [mg] | 10–300 mg |
| --- | --- |
| dimethylpolysiloxane [mg] | 0.3–10 mg |
| glycerylmonostearate [mg] | 0.01–0.5 mg |
| sorbitanmonopalmitate [mg] | 0.08–2.5 mg |
| sucrose monopalmitate [mg] | 0.01–0.5 mg |
| water [mg] | 12–18 mg. |

6. Method of claim 1 wherein the composition is formed corresponding to the following formulation

| [bromure d'otilonium] otilonium bromide [mg] | 150 mg |
| --- | --- |
| dimethylpolysiloxane [mg] | 5 mg |
| glycerylmonostearate [mg] | 0.25 mg |
| sorbitanmonopalmitate [mg] | 1.25 mg |
| sucrose monopalmitate [mg] | 0.25 mg |
| water [mg] | 15 mg. |

7. Method of claim 1 wherein the composition is formed substantially at the moment of use by combining sterile water with a previously prepared dry mixture of the active principle and the antifoaming and emulsifying excipients.

8. Method of claim 7 wherein the dry mixture is stored in a storage container in conserved dry state therein and the sterile water is stored in a solvent vial, and the water is transferred from the vial to the container to form a solution substantially at the moment of use.

9. Method of claim 7 wherein the dry mixture is a powder prepared by absorbing on the active principle a solution of the excipients in an inert solvent and then drying the mixture until the solvent has been essentially completely eliminated therefrom.

10. Method of claim 7 wherein the dry mixture is a powder prepared by absorbing on the active principle a melted mixture of the excipients.

11. An endoscopic method for effecting a medical procedure in the digestive or alimentary canal including one of the esophagus, stomach, duodenum, colon, sigma and rectum of a subject for at least one of diagnostic and therapeutic purposes including bioptic sampling and removal of polypoid formations, comprising the steps of prior to effecting the medical procedure preparing a pharmaceutical product containing otilonium bromide and at least one anti-foaming excipient and at least one emulsifying excipient and applying said prepared pharmaceutical product topically by an endoscopic at a selected location inside the gastrointestinal tract of the subject.

12. An endoscopic method according to claim 1, wherein said pharmaceutical product is an aqueous solution.

13. An endoscopic method according to claim 11, wherein said step of preparing a pharmaceutical product includes preparing a composition corresponding to the following formulation:

| [bromure d'otilonium] otilonium bromide | 10–300 mg |
| --- | --- |
| dimethylpolysiloxane | 0.3–10 mg |
| glycerylmonostearate | 0.01–0.5 mg |
| sorbitanmonopalmitate | 0.08–2.5 mg |
| sucrose monopalmitate | 0.01–0.5 mg |
| water | 12–18 [mg] ml. |

14. An endoscopic method according to claim 11, wherein said step of preparing a pharmaceutical product includes preparing a composition corresponding to the following formulation:

| [bromure d'otilonium] otilonium bromide | 150 mg |
| --- | --- |
| dimethylpolysiloxane | 5 mg |
| glycerylmonostearate | 0.25 mg |
| sorbitanmonopalmitate | 1.25 mg |
| sucrose monopalmitate | 0.25 mg |
| water | 15 [mg] ml. |

15. An endoscopic method according to claim 11, wherein said step of preparing a pharmaceutical product includes forming the pharmaceutical product substantially at the moment of use by combining sterile water with a previously-prepared dry mixture of otilonium bromide and at least one anti-foaming excipient and at least on emulsifying excipient.

16. An endoscopic method according to claim 15, wherein the dry mixture is stored in a storage container in conserved dry state therein and the sterile water is stored in a solvent vial and said sterile water is transferred from the vial to the container to form the pharmaceutical product substantially at the moment of use.

17. A method according to claim 15, wherein the dry mixture is a powder prepared by absorbing on the otilonium bromide a solution of at least one anti-foaming excipient and at least one emulsifying excipient in an inert solvent and then drying the mixture until the solvent has been essentially completely eliminated therefrom.

18. An endoscopic method according to claim 15, wherein the dry mixture is a powder prepared by absorbing on the otilonium bromide a melted mixture of at least one anti-foaming excipient and at least one emulsifying excipient.

19. An endoscopic method according to claim 11, wherein the prepared pharmaceutical product is applied by an endoscopic instrument which is also, subsequently used for one of diagnostic or therapeutic purposes.

* * * * *